(12) United States Patent
Mercola et al.

(10) Patent No.: US 6,475,781 B1
(45) Date of Patent: Nov. 5, 2002

(54) TRANS-DOMINANT SUPPRESSOR GENES FOR OLIGOMERIC PROTEINS

(75) Inventors: Mark K. Mercola, Newton, MA (US); Prescott L. Deininger, New Orleans, LA (US); Charles D. Stiles, Newton Centre, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 08/171,384

(22) Filed: Dec. 21, 1993

Related U.S. Application Data

(63) Continuation-in-part of application No. 07/846,972, filed on Mar. 6, 1992, now abandoned, which is a continuation of application No. 07/525,245, filed on May 17, 1990, now abandoned.

(51) Int. Cl.$^7$ .......................... C12N 5/06; C07H 19/207
(52) U.S. Cl. .................. 435/325; 536/23.1; 536/23.5; 536/23.51; 435/320.1; 435/91.1; 435/91.33; 435/91.4; 435/91.41; 435/91.42; 435/91.5; 435/235.1; 435/252.3; 435/254.11; 424/93.1; 424/93.2; 424/93.21
(58) Field of Search .............................. 536/23.1, 23.5, 536/23.51; 435/320.1, 172.3, 91.1, 91.33, 91.4, 91.41, 91.42, 91.5, 235.1, 252.3, 240.2, 254.11, 325, 455; 424/89, 93 R, 93 A, 93 T, 93.1, 93.21, 93.2; 935/10, 11, 13, 22, 31, 32, 68, 70, 72

(56) References Cited

U.S. PATENT DOCUMENTS

| 4,740,461 | A | * | 4/1988 | Kaufman |
| 4,766,073 | A | | 8/1988 | Murray et al. |
| 4,847,201 | A | | 7/1989 | Kaswasaki et al. |

FOREIGN PATENT DOCUMENTS

| WO | WO 91/11514 | 8/1991 |

OTHER PUBLICATIONS

*Webster's II. New Riverside University Dictionary* 1984, Houghton Mifflin, Co. Boston, MA. p. 93, 779, 1319.*

Singleton et al. (eds). 1987. in: *Dictionary of Microbiology and Molecular Biology.* (Second edition.) John Wiley & Sons., Chichester, G.B. p. 573 and 955.*

Johnsson et al. 1984. EMBO J. 3, 921–928.*

Antoniades et al., Purification of Human Platelet–derived Growth Factor, Proc. Natl. Acad. Sci. USA 76:1809–1813, 1979.

Ausubel et al., (eds.) 1988 in: Current Protocols in Molecular Biology, Greene Publishing Assoc. & Wiley Inter Science pp. 8.0.1–8.1.4.

Betsholtz et al., cDNA Sequence and Chromosomal Localization of Human Platelet–derived Factor A–chain and its Expression in Tumour Cell Lines, Nature 320:695–699, 1986.

Bowen–Pope et al., Sera and Conditioned Media Contain Different Isoforms of Platelet–derived Growth Factor (PDGF) which Bind to Different Classes of PDGF Receptor, J. Biol. Chem. 264:2502–2508, 1989.

Bywater et al., Expression of Recombinant Platelet–Derived Growth Factor A– and B–Chain Homodimers in Rat–1 Cells . . . Protein Processing and Autocrine Effects, Mol. Cell. Biol. 8:2753–2762, 1988.

Curran et al., Fos and Jun: The AP–1 Connection, Cell 55:395–397, 1988.

Damm et al., Protein Encoded by V–erbA Functions as a Thyroid–Hormone Receptor Antagonist, Nature 339:593–597, 1989.

Finlay et al., The p53 Proto–Oncogene Can Act as a Suppressor of Transformation, Cell 57:1083–1093, 1989.

Friedman et al., Expression of a Truncated Viral Trans–activator Selectively Impedes Lytic Infection by its Cognate Virus, Nature 335:452–454, 1988.

Giese et al., The Role of Individual Cysteine Residues in the Structure and Function of the v–sis Gene Product, Science 236:1315–1318, 1987.

Green et al., Mutational Analysis of HIV–1 Tat Minimal Domain Peptides: Identification of Trans–Dominant Mutants that Suppress HIV–LTR Driven Gene Expression, Cell 58:215–223, 1989.

Hames et al., (eds.) 1988 in: Transcription and Splicing. IRL–Press, Oxford, G.B. pp. 1–42.

Heldin et al., Dimerization of B–type Platelet–derived Growth Factor Receptors Occurs after Ligand Binding and is Closely Associated with Receptor Kinase Activation, J. Biol. Chem. 264:8905–8912, 1989.

Heldin et al., Platelet–derived Growth Factor: Purification and Partial Characterization, Proc. Natl. Acad. Sci. USA 76:3722–3726, 1979.

Herskowitz, Functional Inactivation of Genes by Dominant Negative Mutations, Nature 329:219–222, 1987.

Hope et al., Functional Dissection of a Eukaryotic Transcriptional Activator Protein, GCN4 of Yeast, Cell 46:885–894, 1986.

(List continued on next page.)

Primary Examiner—Christopher S. F. Low
(74) Attorney, Agent, or Firm—Fish & Richardson P.C.

(57) ABSTRACT

The invention features two methods for making eucaryotic trans-dominant suppressor genes encoding polypeptide translation products capable of suppressing the activity of a growth factor that requires an oligomeric state for function, suppressor genes made by the methods, protein products of the suppressor genes, and methods for using these genes and protein products.

10 Claims, 12 Drawing Sheets

OTHER PUBLICATIONS

Madisen et al., Transforming Growth Factor–β2: cDNA Cloning and Sequence Analysis, DNA 7:1–8, 1988.

Malim et al., Functional Dissection of the HIV–1 Rev Trans–Activator–Derivation of a Trans–Dominant Repressor of Rev Function, Cell 58:205–214, 1989.

Mercola et al., Platelet–Derived Growth Factor A Chain is Maternally Encoded in Xenopus Embryos, Science 241:1223–1225, 1988.

Mercola et al., Dominant–negative Mutants of a Platelet–derived Growth Factor Gene Genes & Development 4:2333–2341, 1990.

Prockop, Mutations in Collagen Genes, J. Clin. Invest. 75:783–787, 1985.

Sauer et al., Identification of Nonessential Disulfide Bonds and Altered Conformations in the v–sis Protein, a Homolog of the B Chain of Platelet–Derived Growth Factor, Mol. Cell. Biol. 8:1011–1018, 1988.

Seifert et al., Two Different Subunits Associate to Create Isoform–specific Platelet–derived Growth Factor Receptors, J. Biol. Chem. 264:8771–8778, 1989.

Shamah et al., Dominant–Negative Mutants of Platelet–derived Growth Factor Revert the Transformed Phenotype of Human Astrocytoma Cells, Mol. Cell. Biol. 13:7203–7212, 1993.

Singleton et al., (eds.) 1989 in Dictionary of Microbiology and Molecular Biology, John Wiley & Sons. Chichester G.B. pp. 261, 457, 573.

Stryer, Biosynthesis of Amino Acids and Heme, 1975 in: Biochemistry, W.H. Freeman and Co. pp. 503–527.

Triezenberg et al., Functional Dissection of VP16, the Trans– activator of Herpes Simplex Virus Immediate Early Gene Expression, Gene & Development 2:718–729, 1988.

Wachsman et al., HTLV X Gene Mutants Exhibit Novel Transcriptional Regulatory Phenotypes, Science 235:674–677, 1987.

Yarden et al., Epidermal Growth Factor Induces Rapid, Reversible Aggregation of the Purified Epidermal Growth Factor Receptor, Biochemistry 26:1443–1451, 1987.

Armelin et al., Functional Role for c–myc in Mitogenic Response to Platelet–derived Growth Factor, Nature 310:655–660, 1984.

Bejcek et al., The v–sis Oncogene Product but not Platelet–derived Growth Factor (PDGF) A Homodimers Activate . . . Intracellularly and Initiate Cellular Transformation, J. Biol. Chem. 267:3289–3293, 1992.

Bejcek et al., Transformation by v–sis Occurs by an Internal Autoactivation Mechanism, Science 245:1496–1499, 1989.

Betsholtz et al., Efficient Reversion of Simian Sarcoma Virus–transformation and Inhibition of Growth Factor–induced Mitogenesis by Suramin, Proc. Natl. Acad. Sci. USA 83:6440–6444, 1986.

Fleming et al., Amplification and/or Overexpression of Platelet–derived Growth Factor receptors and Epidermal Growth Factor Receptor in Human Glial Tumors, Cancer Research 52:4550–4553, 1992.

Fleming et al., Autocrine Mechanism for v–sis Transformation Requires Cell Surface Localization of Internally Activated Growth Factor Receptors, Proc. Natl. Acad. Sci. USA 86:8063–8067, 1989.

Hermansson et al., Endothelial Cell Hyperplasia in Human Glioblastoma: Coexpression of mRNA for Platelet–derived . . . Receptor Suggests Autocrine Growth Stimulation, Proc. Natl. Acad. Sci. USA 85:7748–7752, 1988.

James et al., Clonal Genomic Alterations in Glioma Malignancy Stages, Cancer Research 48:5546–5551, 1988.

Keating and Williams, Autocrine Stimulation of Intracellular PDGF Receptors in v–sis Transformed Cells, Science 239:914–916, 1988.

LaRochelle et al., A Novel Mechanism Regulating Growth Factor Association with the Cell Surface: Identification of a PDGF Retention Domain, Genes & Development 5:1191–1199, 1991.

Mercola et al., Selective Expression of PDGF A and Its Receptor During Early Mouse Embryogenesis, Developmental Biology 138:114–122, 1990.

Nister et al., Differential Expression of Platelet–derived Growth Factor Receptors in Human Malignant Glioma Cell Lines, J. Biol. Chem. 266:16755–16763, 1991.

Pardridge, Receptor–Mediated PeptideTransport Through the Blood–Brain Barrier, Endocrine Reviews 7:314–330, 1986.

Risser and Pollack, A Nonselective Analysis of SV40 Transformation of Mouse 3T3 Cells, Virology 59:477–480, 1974.

Singh et al., Phylogenetic Analysis of Platelet–derived Growth Factor by Radio–receptor Assay, J. Cell Biology 95:667–671, 1982.

Zhan and Goldfarb, Growth Factor Requirements of Oncogene–Transformed NIH 3T3 and BALB/c 3T3 Cells Cultured in Defined Media, Molecular and Cellular Biology 6:3541–3544, 1986.

* cited by examiner

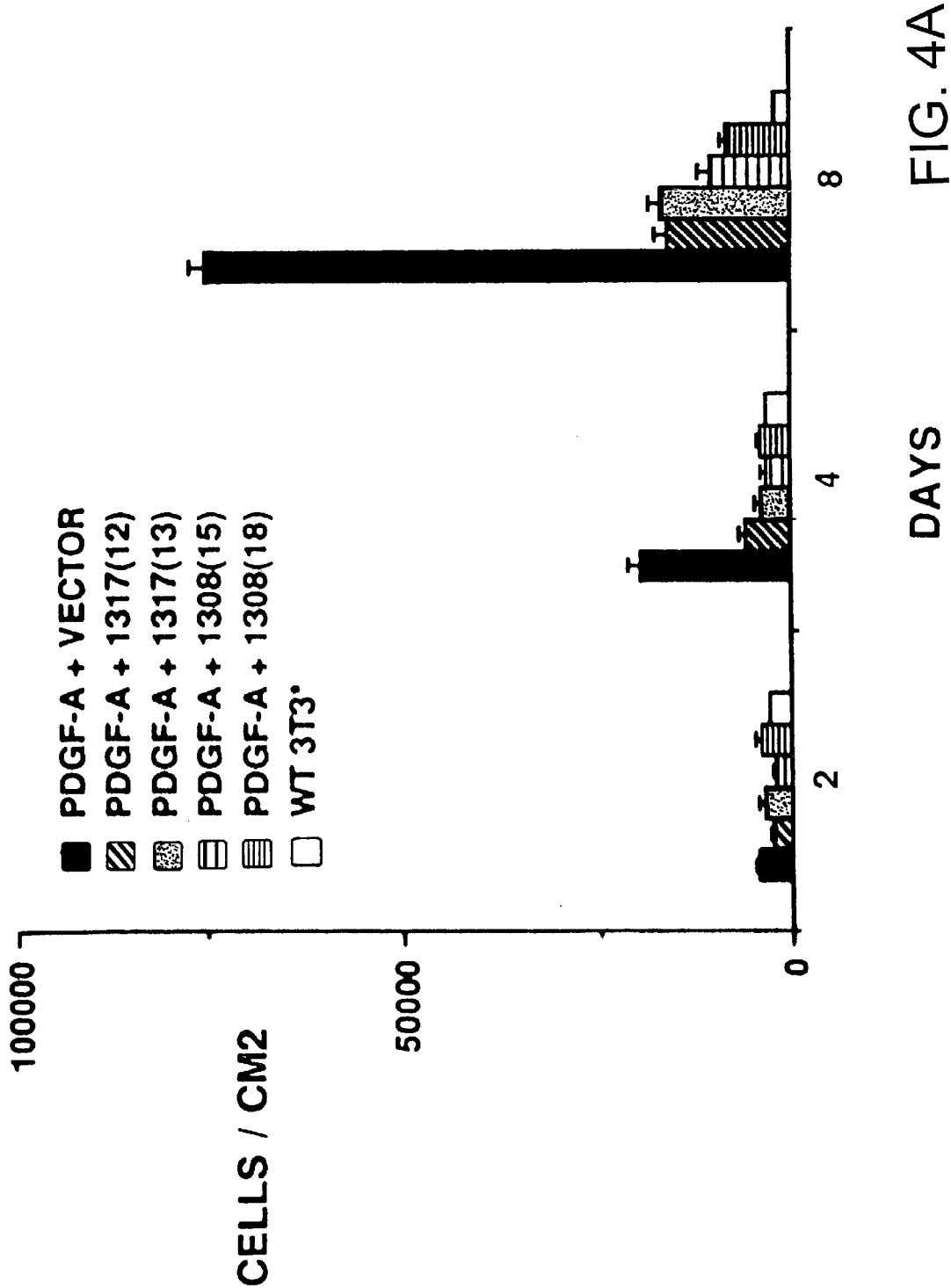

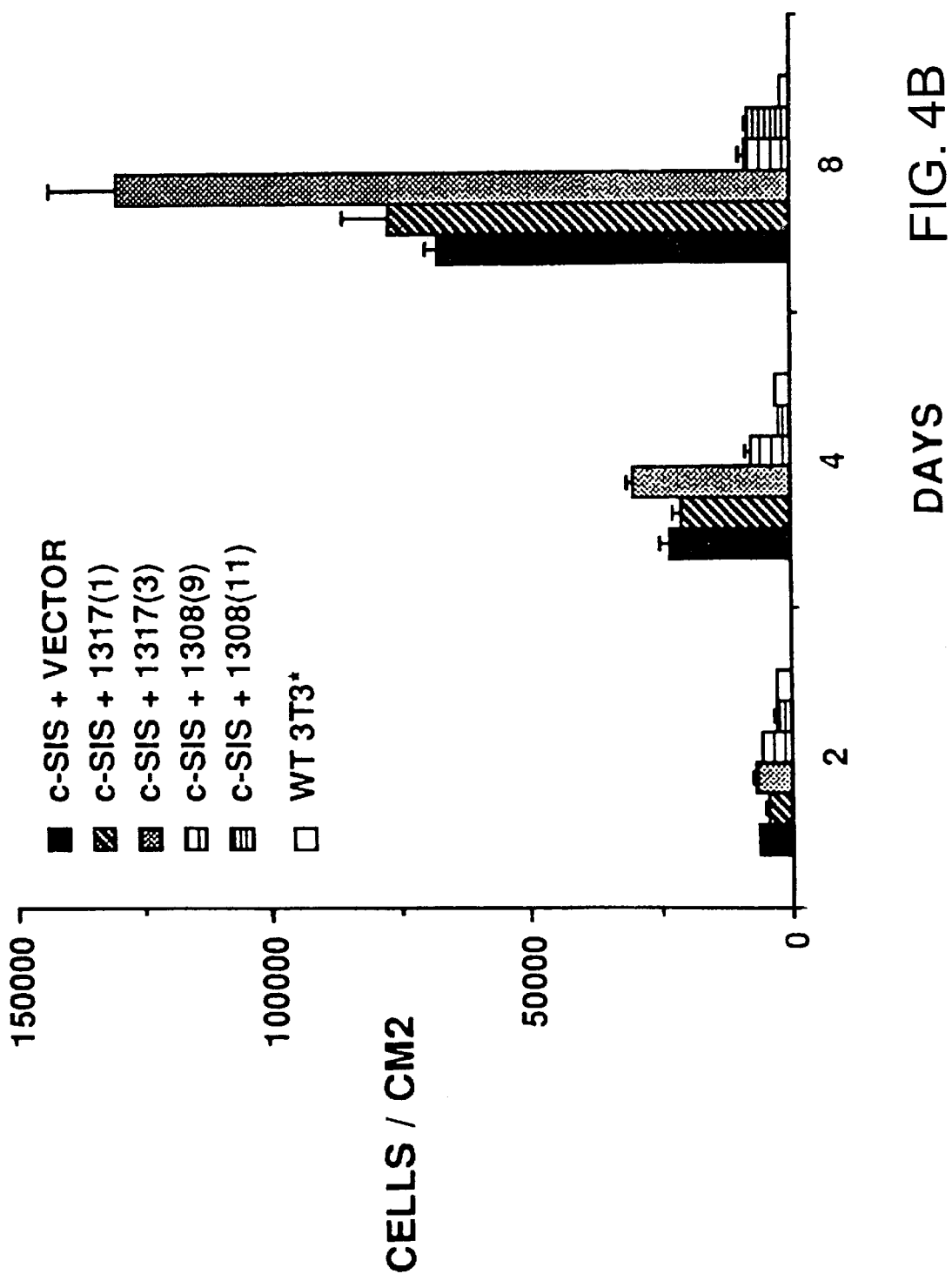

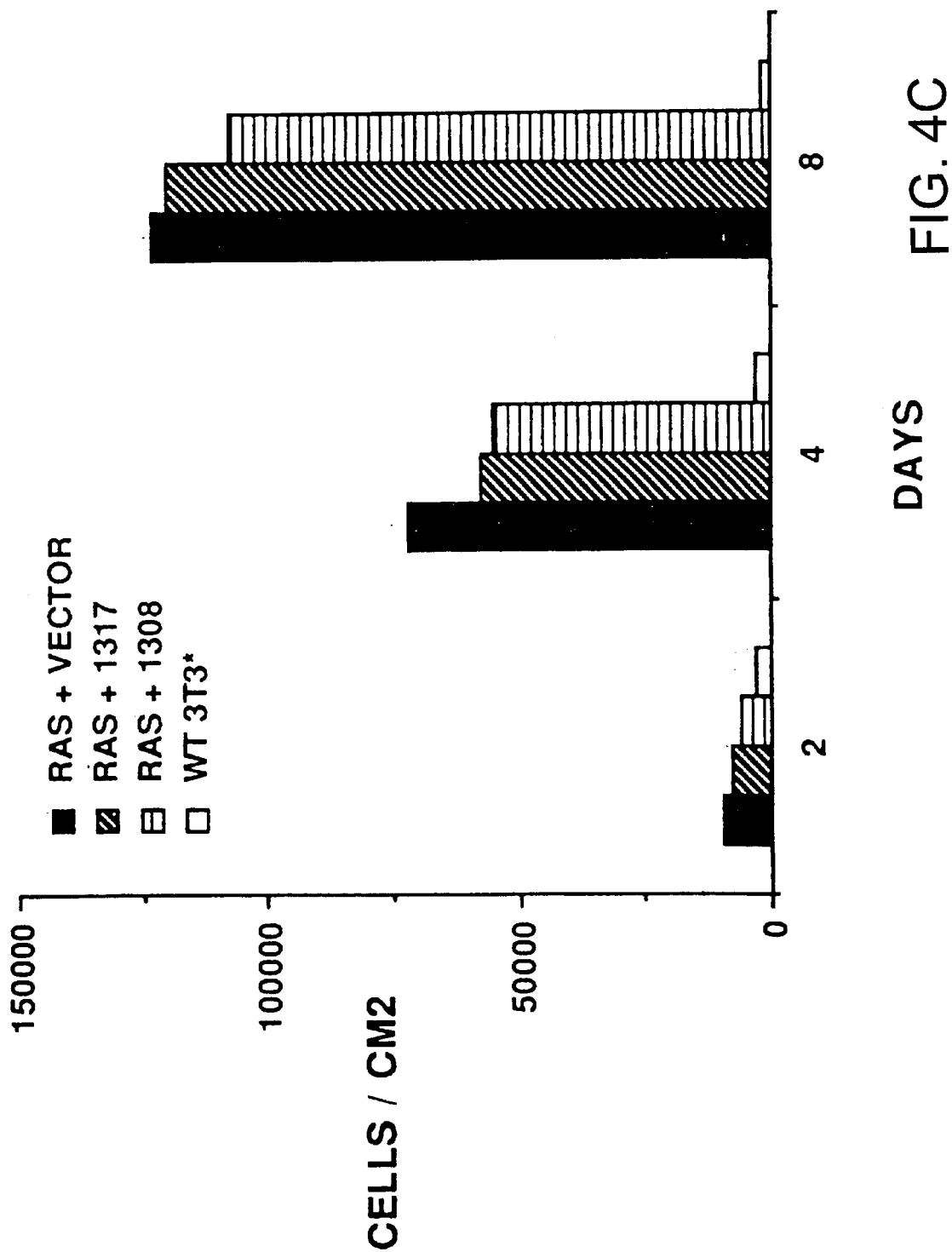

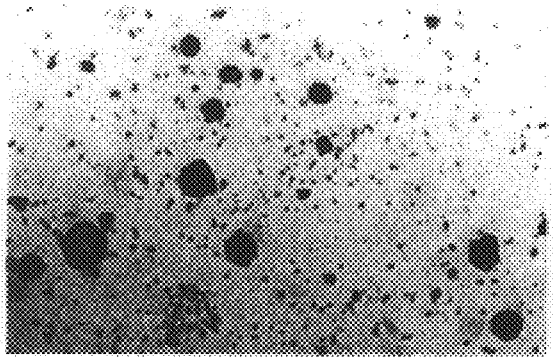 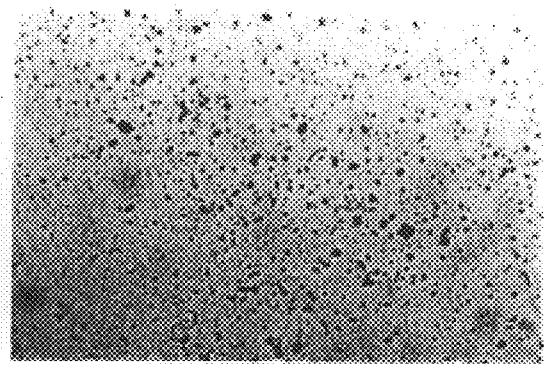 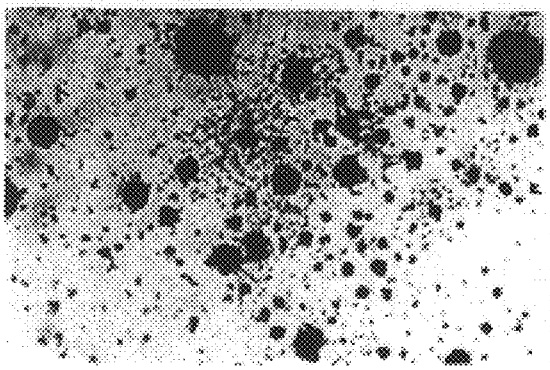 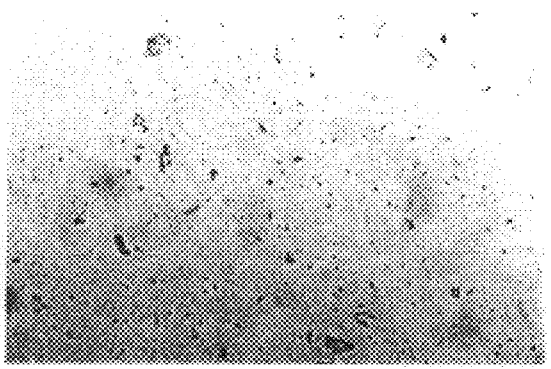 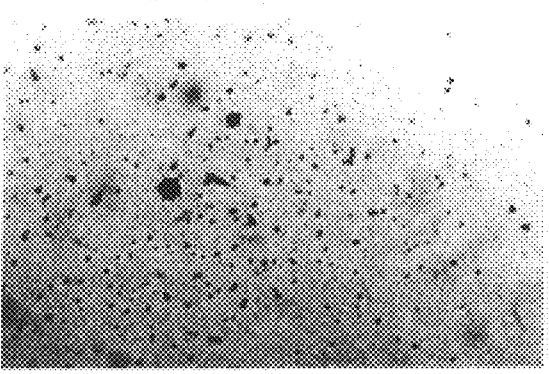 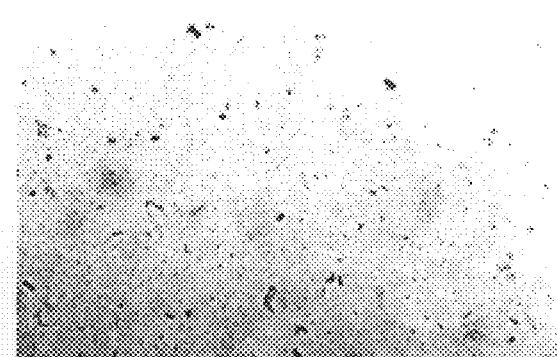
FIG. 6

TRANS-DOMINANT SUPPRESSOR GENES FOR OLIGOMERIC PROTEINS

This application is a continuation-in-part of U.S. Ser. No. 07/846,972, filed Mar. 6, 1992, now abandoned which is a file-wrapper-continuation of U.S. Ser. No. 07/525,245, filed May 17, 1990 now abandoned.

This invention was funded in part by the U.S. Government, and the Government has certain rights in this invention.

BACKGROUND OF THE INVENTION

The invention relates to trans-dominant suppressor genes.

Naturally occurring dominant suppressor genes are known that trigger substantial phenotypic alterations in eucaryotic cells and tissues. Herskowitz (Nature 329:219–222, 1987) has proposed that the natural process can be mimicked by altering a cloned gene so that it encodes a mutant product, capable of inhibiting the wildtype gene product in a cell, thus causing the cell to be deficient in the function of that gene product. Malin et al. (Cell 58:205–214, 1989) and Green et al. (Cell 58:215–223, 1989) performed mutational analyses of two HIV-1 trans-activators essential for viral replication and obtained results which they attributed to effects of the sort described by Herskowitz.

One common, naturally occurring dimeric protein is platelet derived growth factor (PDGF), first recognized and purified from human blood platelets. PDGF has been isolated from a wide variety of cells and tissues of numerous eucaryotic species. The two known PDGF subunits, A and B, are expressed from separate genes and are active as either homo or heterodimers. Dimerization occurs through disulfide linkage between cysteine residues on the individual subunits. The positioning of these residues is conserved between the A and B chains, and between species at least as divergent as human and Xenopus. Four of the eight cysteines residues on each subunit chain are believed to be essential for catalytic activity. The initial translation product of the PDGF A and B genes is a "preproPDGF". A hydrophobic leader sequence (the "pre" sequence) and a substantial length of N-terminal material (the "pro" sequence) are removed by proteolytic cleavage to generate the mature form of a PDGF subunit.

SUMMARY OF THE INVENTION

The invention features two methods for making eucaryotic trans-dominant suppressor genes. A "eucaryotic trans-dominant suppressor gene", as defined herein, is a gene encoding a polypeptide translation product capable of suppressing the activity of a eucaryotic protein that requires an oligomeric state for function, by forming an inactive oligomer with a wildtype subunit of the protein and thereby preventing that wildtype subunit from forming an active dimer with a second wildtype subunit. The methods are particularly useful for producing a trans-dominant suppressor gene that encodes an inactive subunit of a eucaryotic growth factor and thus suppresses the activity of that growth factor.

The first method involves providing a nucleic acid encoding a subunit of the growth factor, the subunit being one that is initially synthesized containing extraneous peptide material which is subsequently removed by cleavage at a proteolytic cleavage site to generate the mature form of the subunit; modifying the base sequence in the nucleic acid in the region encoding the proteolytic cleavage site, so that proteolytic cleavage of the initial translation product of the nucleic acid to the mature form is prevented; and cloning the modified nucleic acid to form the trans-dominant suppressor gene. The modifying step involves either addition or deletion of a codon for an amino acid essential for proteolytic cleavage, or, preferably, substitution of one such essential codon with a codon for a different amino acid. Either way, the reading frame must be preserved. A "proteolytic cleavage site" is an amino acid sequence in the immediate vicinity of a peptide bond that is cleaved by a protease, which amino acid sequence is required for cleavage by the protease. In a preferred embodiment, the proteolytic cleavage site is defined by the sequence -ArgArgLysArg- (SEQ ID NO: 1).

The second method involves providing a nucleic acid encoding a subunit of the growth factor, the subunit being one that is bonded in the oligomeric state by means of a plurality of cysteine residues, at least one of which is essential for the catalytic activity of the protein; modifying in the nucleic acid the codon for one of the cysteine residues essential for the activity of the growth factor, so that another amino acid is substituted for the one cysteine residue, the codon for at least one cysteine residue remaining unmodified; and cloning the modified nucleic acid to form the trans-dominant suppressor gene. In a preferred embodiment, the cysteine residue modified in this method is the third cysteine residue of the mature form of PDGF A.

In preferred embodiments, the growth factor is a member of the platelet derived growth factor (PDGF) superfamily, e.g. PDGF A or B, or vascular endothelial cell growth factor (VEGF); colony stimulating factor I (CSF-I); or a member of the transforming growth factor beta (TGF-β) superfamily, e.g. TGF-β1 or TGF-β2.

In another aspect, the invention features a eucaryotic trans-dominant suppressor gene. In one embodiment, the eucaryotic trans-dominant suppressor gene encodes a protein translation product that is a mutant form of a PDGF subunit having a modification in the amino acid sequence corresponding to the proteolytic cleavage site of the PDGF subunit which prevents cleavage at the site. In another embodiment, the eucaryotic trans-dominant suppressor gene encodes a mutant form of a PDGF subunit in which one of the cysteine residues essential for the mitogenic activity of PDGF is replaced with a different amino acid, and at least one other cysteine residue remains unmodified. In other embodiments, the growth factor is TGF-β1, TGF-β2, CSF-I, or VEGF. The invention also features the protein translation products of the eucaryotic trans-dominant suppressor genes of the invention. These protein translation products also are referred to as "dominant suppressor proteins" or "dominant negative mutants".

In another aspect, the invention features a vector containing the trans-dominant suppressor gene, which may be operably linked to a functional promoter. A "vector" is defined as a replicable nucleic acid construct. Vectors are used in the invention to amplify and/or express nucleic acid encoding the dominant suppressors. An expression vector is a replicable construct in which a nucleic acid sequence encoding the dominant suppressor protein is operably linked to suitable control sequences capable of effecting expression of the dominant suppressor protein in a cell. The need for such control sequences will vary depending upon the cell selected and the transformation method chosen. Generally, control sequences include a transcriptional promoter and/or enhancer, a sequence encoding suitable mRNA ribosomal binding sites, and sequences which control the termination of transcription and translation. Amplification vectors do not require expression control domains. The only sequences required in an amplification vector are one which confers the ability to replicate in a cell, which is usually an origin of replication, and a selection gene to facilitate recognition of transformants. A gene and a promoter and/or enhancer are defined as being "operably linked" if the promoter and/or enhancer controls the transcription of the gene. A "functional promoter" is defined as a region of DNA involved in binding RNA polymerase to initiate transcription. Vectors of the invention include, but are not limited to, plasmid vectors and viral vectors. Preferred viral vectors of the invention are those derived from retroviruses, adenovirus, adeno-associated virus, SV40 virus, or herpes viruses.

The invention also features a cell containing a eucaryotic trans-dominant suppressor gene. In one embodiment, the cell expresses the eucaryotic trans-dominant suppressor gene. The cell can be either a procaryotic cell, e.g. an *Escherichia coli* cell, or a eucaryotic cell. Eucaryotic cells that can be used in the invention include, but are not limited to, Cos, CHO, and Sf9 cells. In the case of a eucaryotic cell, the gene may or may not be integrated into the genome of the cell. Also included in the invention is an essentially homogeneous population of procaryotic or eucaryotic cells, each of which contains a eucaryotic trans-dominant suppressor gene.

In a related aspect, the invention features a method of producing a dominant suppressor protein by culturing a cell that expresses a trans-dominant suppressor gene under suitable conditions for expressing the gene, and isolating recombinant protein so produced (Sambrook et al., Molecular Cloning: A Laboratory Manual, 2nd, Cold Spring Harbor Laboratory Press, 1989). The cell used in this method can be either procaryotic or eucaryotic.

In another aspect, the invention features a therapeutic composition containing the trans-dominant suppressor gene of the invention in a pharmacologically acceptable carrier (e.g. physiological saline). In a preferred embodiment, the trans-dominant suppressor gene in the therapeutic composition is in a viral genome within a viral particle. In a related aspect, the invention features a therapeutic composition containing the dominant suppressor protein of the invention in a pharmacologically acceptable carrier.

In another aspect, the invention features a transgenic non-human animal whose germ cells, somatic cells, or both contain one or more copies of the trans-dominant suppressor gene that was introduced by artifice into the animal, or an ancestor of the animal, at an embryonic stage. Preferred transgenic animals include laboratory animals such as mice. In a preferred embodiment, the trans-dominant suppressor gene in the transgenic animal is under the control of a tissue-specific promoter.

In a final aspect, the invention features a method for inhibiting unwanted cell proliferation in a patient, which proliferation is stimulated at least in part by the presence of an autocrine or paracrine loop, by administering to the patient one of the therapeutic compositions of the invention, as described above. The patients that can be treated by this method include, but are not limited to, mammals such as humans, cows, horses, pigs, dogs, cats, sheep, goats, rabbits, rats, guinea pigs, hamsters, and mice. The unwanted cell proliferation that can be inhibited by the methods of the invention includes, but is not limited to, cancer (e.g. malignant astrocytoma, sarcoma, glioma, lung carcinoma, mammary carcinoma, or cervical carcinoma) and that which is related to, for example, atherosclerosis, coronary artery disease, or rheumatoid arthritis.

Other features and advantages of the invention will be apparent from the following detailed description, the drawings, and from the claims.

BRIEF DESCRIPTION OF THE DRAWING

FIGS. 4A–4C are graphs of the growth of PDGF-A (FIG. 4A), PDGF-B (c-sis)(FIG. 4B), and Ha-ras (FIG. 4C) transformed cells transfected with dominant negative mutants of PDGF. Numbers in parentheses represent identification of different clonal cell lines. Each value (with the exception of Ha-ras values) represents the average +/− the standard error of the mean of two independent growth curve experiments.

FIG. 6 is an analysis of the anchorage-independent growth of PDGF-A and c-sis transformed Balb/c3T3 cells transfected with the dominant negative mutants indicated.

DETAILED DESCRIPTION

Figure 1:
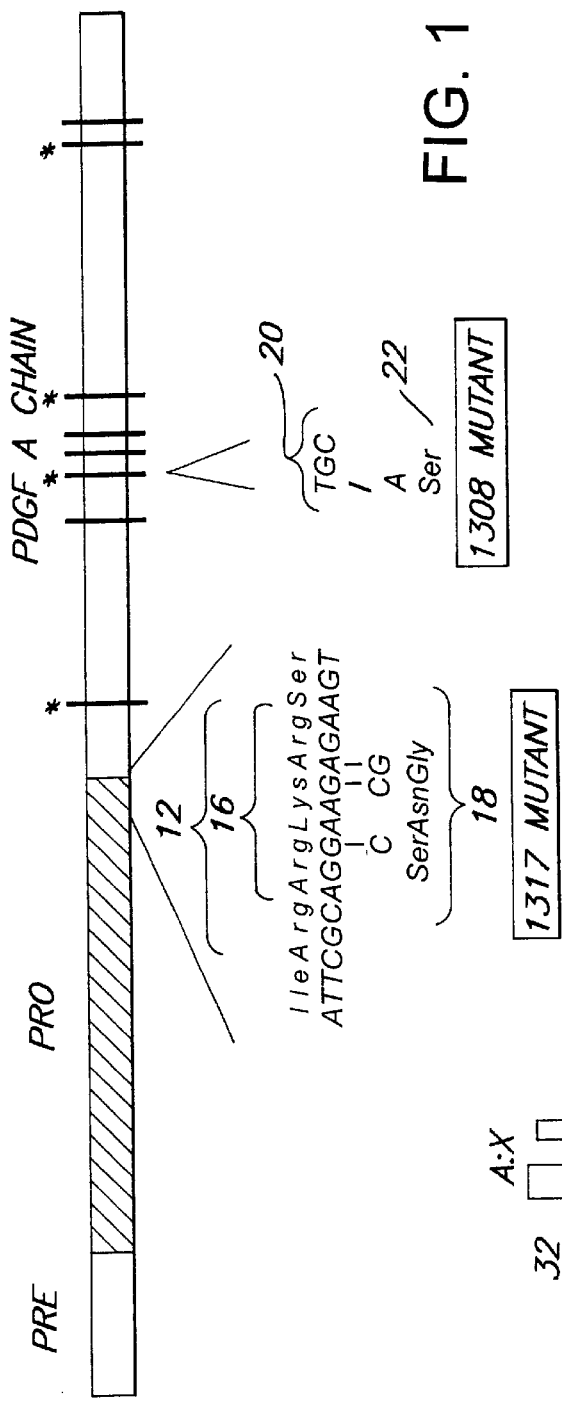
FIG. 1 is a representation of the murine preproPDGF A chain and sites of directed mutagenesis. The amino acid sequence Ile Arg Arg Lys Arg Ser is assigned SEQ ID NO:6 and the nucleotide sequence ATTCGCAGGAAGAGAAGT is assigned SEQ ID NO:7.

The invention enables the preparation of trans-dominant suppressor genes encoding mutant subunits of two different categories of oligomeric proteins.

In one category, the protein is composed of subunits at least one of which is initially synthesized containing extraneous peptide material. This extraneous material sequence is subsequently removed during normal processing by cleavage at a proteolytic cleavage site to generate the mature form of the subunit. According to the invention, DNA encoding the initial form of the indicated subunit is cloned, and the base sequence of the DNA in the region encoding the proteolytic cleavage site is modified so that processing of the translation product of the gene to the mature form of the subunit is prevented.

In the other category, the oligomeric protein is one in which the monomers are bonded together by at least two disulfide bonds, at least one of which is essential for the catalytic activity of the protein. In the method of the invention, DNA encoding one of the subunits is cloned, and the base sequence of the DNA in the region encoding a cysteine residue essential for catalytic activity is modified. The codon for at least one cysteine residue remains unmodified.

The resulting translation product of the altered gene of either category will still bind to wildtype subunits; yet the resultant oligomers will be inactive. The protein product of the suppressor gene thus serves to suppress the wildtype activity.

Dominant suppressor genes can be prepared that will inhibit the activity of any oligomeric protein in which either, one subunit is initially synthesized containing a subsequently cleaved extraneous sequence (e.g., a "pro" sequence or an internal sequence), or the monomers of the protein are bonded together by at least two disulfide bonds, at least one of which is essential for the catalytic activity of the protein. These proteins include, but are not limited to, PDGF, members of the transforming growth factor beta (TGF-β) family of growth factors, colony stimulating factor 1 (CSF-I), vascular endothelial cell growth factor (VEGF), several growth factor receptors, and several transcription factors. The following example describes the construction of dominant suppressor genes of PDGF.

EXAMPLE I

Construction of the Dominant Suppressor Genes

Two types of dominant suppressor PDGF A genes were constructed as follows. A fragment spanning the open reading frame of the clone F9A5 (Mercola et al., Develop. Biol. 138:114–122, 1990), which codes for the entire murine preproPDGF A chain protein, was cloned into the EcoR1 site of the bluescript vector, pBSKS+ (Stratagene). Single-stranded DNA was prepared using M13K07 (Promega Corp., Madison, Wis.) as the helper phage. Site-directed mutagenesis was carried out by the method of Kunkel et al. (Methods of Enzymology, R. Wu and L. Grossman, eds. 154:367–382, 1987) and resulted in the isolation of two mutants carrying dominant suppressor genes, 1317 and 1308.

For mutant 1317, the modification involved was a change in the proteolytic cleavage site for processing the prepro form of the murine PDGF A chain to the mature form. Referring to FIG. 1, the tetra basic amino acid sequence -ArgArgLysArg- (12) (SEQ ID NO: 1) was selected as the target sequence for the protease that converts proPDGF A to PDGF A on the basis of observations that the amino terminus of mature PDGF A begins with the amino acid -Ser- (14) immediately to the carboxyl side of this tetra basic residue and that a string of three to five basic amino acids is found in a comparable position within the reading frames of other growth factors that undergo similar processing, notably PDGF B, TGF-β1, TGF-β2, CSF-1, and VEGF. Site directed mutagenesis was used to alter the sequence - ArgLysArg- (16) at this putative proteolytic cleavage site to -SerAsnGly- (18). Changing the amino acid sequence in this drastic manner served to prevent removal of the propeptide.

For mutant 1308, the modification involved was a change in the codon for one of four essential cysteine residues in the PDGF A chain. Again referring to the FIG. 1, site directed mutagenesis was used to alter the codon TGC (20) for the third cysteine residue in the chain to AGC, to code for serine (22).

As mentioned above, other growth factors which are appropriate for the application of this technology include members of the TGF-β superfamily, CFS-1, and VEGF. All members of the TGF-β superfamily, CFS-1, and VEGF are growth factors which function in a dimeric state like PDGF. Dominant suppressor mutants of TGF-β1 and TGF-β2 have been constructed by disrupting basic amino acids near the propeptide processing region in a manner described for the PDGF A 1317 mutation. TGF-β1 contains the following amino acid sequence at the processing site: -SerArgHisArgArgAla(SEQ ID NO: 2). This sequence was changed to -SerGlnHisSerGlyAla- (SEQ ID NO: 3). TGF-β2 contains the following sequence at its processing site: -ArgArgLysLysArgAla- (SEQ ID NO: 4). This sequence was changed to -ArgGlnAsnGlnGlyAla- (SEQ ID NO: 5). In both cases, the modification was effective in suppressing the corresponding growth factor.

Any conventional method of site directed mutagenesis, including amino acid substitution, addition or deletion, that will not disrupt the reading frame of the resulting cDNA, is appropriate for implementing dominant suppressor gene technology. Polymerase chain reaction (PCR) methods (Erlich, PCR Technology, Stockton Press, 1989) can also be used.

EXAMPLE II

Characterization of Dominant Negative Mutants of PDGF A

In order to analyze the proteins encoded by the dominant suppressor genes, the two mutant PDGF subunit cDNAs and the wildtype PDGF A cDNA were cloned into the pMT2 expression vector, and each of these constructs was transfected into COS cells. The COS cell cultures were incubated with $^{35}$S-cysteine to label the translation products, and the conditioned media were analyzed by immunoprecipitation with PDGF A chain-specific antibodies. The wildtype PDGF A cDNA produces a species that is consistent with previous determinations of the molecular weight of PDGF A (16 kd).

Co-transfection of COS cells with equal amounts of the wildtype and 1317 mutant constructs produces a major band at 38 kd on non-reducing gels, showing that a 1317/wildtype heterodimer is formed in which the wildtype protein is properly processed. Co-transfection of wildtype with the 1308 construct did not result in any obvious structural changes. However, the abundance of the wildtype protein was decreased substantially. A series of transfections carried out with a fixed amount of the wildtype construct along with increasing amounts of the 1308 mutant showed that increasing amounts of the mutant resulted in a steady decrease in the amount of the wildtype protein expressed in the conditioned media. The mutant and the mutant/wildtype dimers appear to be subject to rapid degradation.

The biological inactivity of the protein products of the mutant genes was demonstrated using a bioassay for PDGF. Transfection of 2.5 μg of the mouse wildtype PDGF A, assayed on Balb/c-3T3 cells, resulted in 266 ng/ml of PDGF in the conditioned media. Transfection of 17.5 μg of either of the mutant constructs resulted in less than 1 ng/ml of activity. This level of expression is not significantly above the background level produced from COS cells transfected by the pMT2 expression vector alone.

As a demonstration of the impact of the mutant PDGF products on the biological activity of wildtype PDGF, COS cells were co-transfected with 2.5 μg of the wildtype PDGF A chain construct along with increasing amounts of mutant constructs. Total DNA was adjusted to a constant 20 μg per transfection by addition of the pMT2 vector to minimize variations in transfection efficiency. Transfections with a 3- or 7-fold excess of 1317 DNA relative to wildtype DNA resulted in approximately 5- and 10-fold decreases in activity, respectively. Transfections with the wildtype gene and the 1308 mutant show a similar decrease in PDGF activity. Thus, the processing mutant, 1317, results in formation of a mutant/wildtype heterodimer that is efficiently secreted, but is biologically inactive, while the 1308 mutant appears to destabilize the heterodimer, causing its degradation prior to release from the cells.

The murine PDGF A dominant suppressor can also be used effectively in a wide range of species because the cysteines are highly conserved. This possibility has been confirmed by blocking the biological activity of the *Xenopus laevis* A chain using these mutants. When the open-reading frame from pX01, a Xenopus A chain cDNA clone, is expressed 30 in COS cells along with mutants 1317 and 1308, the mouse PDGF mutants are both effective at suppressing Xenopus PDGF.

Figure 2:
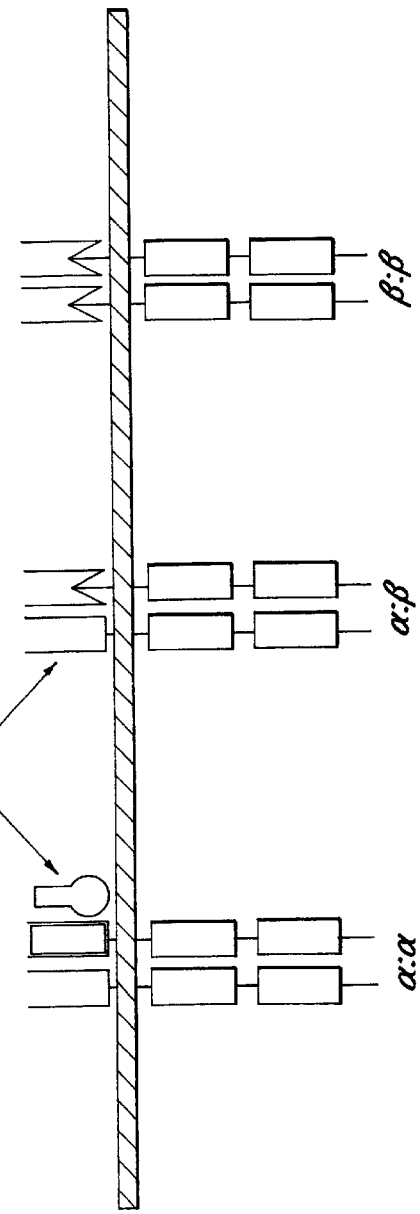
FIG. 2 is a representation of possible interactions between heterodimers of PDGF wildtype and dominant suppressor subunits on the one hand, and PDGF receptor isoforms on the other hand.

In normal cells, monomeric PDGF receptor subunits alpha (α) and beta (β) are in dynamic equilibrium with three receptor isoforms—α:α, α:β, and β:β. In successful PDGF:receptor interactions, each half of a PDGF dimer occupies one-half of a receptor dimer. It is known that in cells that have been stripped of α receptor units, so as to leave only β subunits, PDGF A:B heterodimers are not mitogenic; however, an excess of A:B heterodimer can inhibit the mitogenic response to a nominal dose of a B:B homodimer. Apparently, the B subunit within A:B heterodimers is able to occupy ½ of β:β receptor dimer without activating it and thereby render it useless for a productive interaction with PDGF B:B. For example, referring to FIG. 2, the mutant proPDGF A subunit produced by mutant 1317 is too bulky to occupy the α receptor site. Yet this subunit is able to dimerize with wildtype PDGF A (32). This mutant heterodimer (32) should compete with either PDGF A:A or A:B, to bind to the α receptor.

EXAMPLE III

Therapeutic Uses of Trans-dominant Suppressors

Autocrine loops are established when a ligand, e.g. PDGF, and its receptor, e.g. the PDGF receptor, are expressed in the same cell. In tissue culture, PDGF autocrine loops can both initiate and sustain a transformed phenotype (Bejcek et al., J. Biol. Chem. 267:3289–3293, 1992; Fleming et al., Cancer Res. 52:4550–4553, 1992; Hermanson et al., Proc. Natl. Acad. Sci. USA 85:7748–7752, 1988; Keating et al., Science 239:914–916, 1988).

To document the contribution of autocrine loops to malignant growth, it is necessary to demonstrate that, when the loop is disrupted, normal growth regulation is restored. Existing reagents that antagonize the interaction between a growth factor and its receptor, such as suramin or neutralizing antibodies, function on the outside of the cell. However, recent studies indicate that PDGF autocrine loops can be established within the cell interior in compartments which are poorly accessible to these agents (Bejcek et al., Science 245:1496–1498, 1989; Bejcek et al., J. Biol. Chem. 267:3289–3293, 1992; Fleming et al., Proc. Natl. Acad. Sci. USA 86:8063–8067, 1989; Keating et al., Science 239:914–916, 1988). Perhaps for these reasons, attempts to inhibit the growth of cells transformed by PDGF autocrine loops with surface reagents have yielded mixed results (Betsholtz et al., Proc. Natl. Acad. Sci. USA 83:6440–6444, 1986; Hermanson et al., Proc. Natl. Acad. Sci. USA 85:7748–7752, 19788; James et al., Cancer Res. 48:5546–5551, 1988).

PDGF autocrine and/or paracrine loops have been linked to a number of diseases including lung carcinoma, malignant astrocytoma, glioma, sarcoma, coronary artery disease, cervical carcinoma, mammary carcinoma, atherosclerosis, and hyper-proliferative disorders of connective tissue such as rheumatoid arthritis. It has now been shown that the 1308 and 1317 dominant negative PDGF mutants described above are capable of disrupting PDGF autocrine loops. These studies are described in the Experimental Data section below. Briefly, the mutants were tested in a defined context using PDGF transformed Balb/c 3T3 cells, and then in several human astrocytoma cell lines. The results show that PDGF dominant negative mutants revert the phenotype of PDGF transformed cells and at least some human astrocytomas. These data are consistent with the notion that PDGF autocrine loops are an active factor in the transformed phenotype of these tumors. Thus, the dominant suppressors of the invention can be used to treat patients with diseases caused or exacerbated by PDGF autocrine and/or paracrine loops, or other types of autocrine and/or paracrine interactions.

The dominant suppressors can be administered to patients in the form of protein or nucleic acid. The dominant suppressor proteins of the invention can be produced by any appropriate methods known in the art, including recombinant, chemical, in vivo, and in vitro methods. Recombinant production of dominant suppressors can be carried out by overexpression of the proteins in bacteria (Sambrook et al., Molecular Cloning: A Laboratory Manual, 2nd, Cold Spring Harbor Laboratory Press, 1989). However, many eucaryotic proteins synthesized in bacteria fold incorrectly or inefficiently and consequently exhibit low specific activities. In addition, production of biologically active eucaryotic proteins frequently requires post-translational modifications that are not performed by bacterial cells. Thus, the use of eucaryotic expression systems is often required for the production of functional eucaryotic proteins.

The invention includes the use of any eucaryotic expression system for production of the dominant suppressor proteins. For example, mammalian systems involving the use of SV40- and adenovirus-based expression vectors can be used. These vectors can be used to transfect the dominant suppressor genes into mammalian cells such as Cos cells (Cos cells are available from the American Type Culture Collection, Rockville, Md., ATCC# 1650). Viral vectors also can be used to direct expression of the dominant suppressor proteins in mammalian cell cultures (Sambrook et al., Molecular Cloning: A Laboratory Manual, 2nd, Cold Spring Harbor Laboratory Press, 1989). Another eucaryotic expression system that can be used in the methods of the invention is the baculovirus system (Summers and Smith, "A manual of methods for baculovirus vectors and insect cell culture procedures". *Tex. Agric. Exp. Stn. Bull.* No. 1555, 1987).

The invention includes any methods which accomplish in vivo transfer of foreign genes into somatic tissues. The preferred gene therapy method of the invention involves administration of recombinant viral vectors containing nucleic acids encoding the dominant suppressors. However, the invention also includes any method of transfecting nucleic acids into eucaryotic cells. The nucleic acids can be packaged into viral vectors, non-viral vectors, liposomes, or erythrocyte ghosts. The nucleic acids also can be injected into target tissues in calcium phosphate precipitates or coupled with lipids.

The preferred gene transfer vectors of the invention are those derived from retroviruses. However, the invention also includes the use of any vectors derived from DNA viruses. Preferred DNA viruses include, but are not limited to, herpes simplex virus (HSV) type 1, adenovirus, adenoassociated virus, SV40 virus, and any modified versions of these viruses.

The dominant suppressor genes and proteins of the invention can be administered to patients in pharmacologically acceptable carriers such as physiological saline. The mode of administration will vary, depending on the tissue being treated. Administration may be carried out by direct injection, e.g., by intravenous, intramuscular, or intraperitoneal injection. Alternatively, it may be necessary to administer the treatment surgically to the appropriate target tissue, or nasally in the form of an inhalant.

For the treatment of diseases in the brain, e.g. malignant astrocytoma, the therapeutic compositions of the invention must cross the blood-brain barrier. While this barrier may be effectively bypassed by direct infusion of therapeutic compositions into the brain by surgical methods, it may be preferable to use other methods. For example, therapeutic reagents of the invention which have been modified so as to enhance their transport across the blood-brain barrier can be administered. The transport of a protein across the blood-brain barrier can be enhanced by a number of methods, including conjugating it to various lipophilic compounds, conjugating it to a molecule which is naturally transported across the barrier, or by reducing the overall length of the polypeptide chain (Pardridge, Endocrine Reviews 7:314–330 1986; U.S. Pat. No. 4,801,575).

The therapeutic compositions of the invention can be administered in dosages determined to be appropriate by one skilled in the art. An appropriate dosage is one which effects a reduction in the disease. It is expected that a useful dosage contains between $10^6$ and $10^{14}$ copies of the gene of the invention, or an amount of the protein of the invention that results in a local concentration of 1–1000 ng/ml. The treatment of the invention can be repeated as needed, as determined by one skilled in the art.

EXAMPLE IV

Using a Dominant Suppressor Gene to Create a Transgenic Laboratory Animal which will Serve as a Disease Model for Medical Research The amino acid sequences of the two genes which encode PDGF (PDGF A and PDGF B) have been stringently preserved from humans down through lower vertebrates. The A gene of PDGF is expressed at extremely early times in the development of mammals and amphibians. For these reasons, it is believed that PDGF regulates important processes in normal physiology; however, the true functions of PDGF in vivo have not been established. Using dominant suppressor technology, a permanent strain of a mammal can be created which is unable to produce PDGF. Such a mammal can be used to study the functions of PDGF in vivo and to discover new drugs which might enhance or suppress those functions, as needed. The preferred mammal of the invention is a mouse; however, other laboratory animals such as rats, rabbits, and guinea pigs can be used.

To produce a PDGF deficient mammal, such as a mouse, a PDGF dominant suppressor gene, such as one of the PDGF A mutant cDNAs described above, can be placed downstream of a strong promoter which functions well in mice, such as the SV40 promoter, the cytomegalovirus promoter, or any of several retrovirus LTRs. Other usual features of a transgenic mouse vector (splice donor/acceptor sites and a polyadenylation signal) can also be incorporated into this promoter-driven PDGF A suppressor, and are well-known in the art. Using procedures which are widely in practice, such as microinjection, a permanent strain of transgenic mice which expresses the PDGF suppressor protein in virtually all tissues can be created. Expression of the mutant protein would be of little or no consequence in tissues which do not manufacture PDGF. In mouse tissues which normally produce PDGF, the dominant suppressor protein should inactivate the wildtype PDGF A and/or B chains. (It has been found that the 1317 mutation will suppress wildtype PDGF A activity while the 1308 mutation will suppress both wildtype PDGF A and PDGF B activity.) If PDGF has essential functions at early times in vertebrate embryogenesis, tissue-specific promoters such as plateletfactor 4 can be used which would only be expressed during adult life.

Other Embodiments

From the above description, one skilled in the art can easily ascertain the essential characteristics of the present invention, and without departing from the spirit and scope thereof, can make various changes and modifications of the invention to adapt it to various usages and conditions.

Other embodiments are in the claims set forth below.

Experimental Data

Materials and Methods cDNA plasmid constructs. Full length mouse PDGF-A (Mercola et al., Dev. Biol. 138:114–122, 1990) and human csis (EMBL/GenBank Accession number for c-sis is XO2811) cDNAs were cloned into the EcoRI site of the pMT2 expression vector (Kaufman et al., Mol. Cell. Biol. 9:946–958, 1989) and expressed under the control of the adenovirus major late promoter. The 1308 and 1317 PDGF dominant negative mutants were cloned into the HindIII site of the PLNCX vector (Miller et al., BioTechniques 7:980–990, 1989) and expressed under the control of the cytomegalovirus immediate early promoter. The neomycin resistance gene is expressed by pLNCX; resistance to hygromycin B was conferred to cells by co-transfection with pY3 (Blochlinger et al., Mol. Cell Biol. 4:2929–2931, 1984).

Cell transfections. Transfection of Balb/c 3T3 cells was performed using a calcium phosphate precipitation technique. Approximately 18 hours prior to transfection, $10^6$ cells/dish were plated on 100 mm diameter tissue culture dishes in Dulbecco's Modified Eagle Medium (DMEM; Gibco) supplemented with 10% bovine calf serum (BCS; Hyclone). A mixture of DNA (20 μg of pMT2 constructs with 1 μg of pY3, or 20 μg of pLNCX constructs) in 0.5 ml of 0.125 M $CaCl_2$ was added dropwise to 0.5 ml 2×HBS buffer (280 mM NaCl, 1.5 mM $Na_2HPO_4.7H_2O$, 50 mM HEPES) with constant aeration, and incubated for 30 minutes at room temperature (RT) to facilitate the formation of a calcium phosphate precipitate. The precipitate was added to cells without media for 20 minutes at RT followed by a 4 hour incubation with 4 ml of 10% BCS at 37° C. After removing the precipitate, the cells were shocked with 15% glycerol/1xHBS for three minutes, rinsed twice with phosphate buffered saline (PBS), and grown in 10% BCS. Clonal lines were isolated in the third to fourth week of drug selection with 200 µg/ml hygromycin B (Calbiochem) and/or 500 µg/ml neomycin sulfate (Gibco). Four mm squares of trypsin-soaked Whatman 3 MM filter paper were applied directly to PBS-rinsed cell colonies, incubated for three minutes at 37° C., and transferred to 6-well tissue culture dishes (Falcon) for subsequent clonal expansion.

For the astrocytoma cell lines, transfections were performed with Lipofectin Reagent (Gibco/BRL) as follows. Eighteen hours prior to transfection, $10^6$ cells were plated on fibronectin-coated (1 µg/cm² for 1 hour; Collaborative Biomedical Products) 100 mm diameter tissue culture dishes. Lipofectin was added to DMEM at a concentration of 16 µl/ml and then mixed with an equal volume of DMEM containing DNA (PLNCX constructs) for a final concentration of 8 µl/ml. Cells were rinsed twice with PBS and incubated with 4 ml/dish of the Lipofectin/DNA mixture at 37° C. for 5 hours at which time an equal volume of 10% BCS was added. Drug resistant cultures were selected in 500 µg/ml neomycin sulfate.

Metabolic labelling and immunoprecipitation. Primary clones were first screened for expression of PDGF-A or c-sis mRNA by Northern analysis. One subline expressing abundant PDGF-A mRNA and another expressing abundant c-sis mRNA were metabolically labelled to verify PDGF protein expression. Cells were grown to confluence on five 100 mm diameter tissue culture dishes (Falcon), rinsed twice with cysteine-free DMEM, and incubated with 250 µCi $^{35}$S cysteine (NEN) in 1 ml cysteine-free DMEM for 4 hrs at 37° C. with intermittent rocking. After the conditioned medium (CM) was harvested, the cells were rinsed twice with PBS and lysed with 1 ml RIPA buffer (150 mM NaCl$_4$, 50 mM Tris pH 8.0, 1% Nonidet P-40, 10 mM Deoxycholic acid, 0.1% SDS) containing 1 mM PMSF. The CM and cell lysates (CL) were concentrated in Amicon Centriprep-10 concentrators (10,000 M.W. cutoff) and then clarified by centrifugation before immunoprecipitation.

Immunoprecipitations were performed with a polyclonal mouse PDGF-AA-specific antibody (1:100; Wang et al., Growth Factors 7:279–286, 1992) and a monoclonal human PDGF-BB specific antibody (1:400, Upstate Biotechnology Incorporated, (UBI)). Antibodies were added directly to CL, or with RIPA/PMSF to CM, and incubated for three hours at 4° C. with constant rocking. For competition experiments, 1 µg of unlabelled, recombinant PDGF-AA (UBI) or PDGF-BB (UBI) was added to the CL or CM prior to addition of antibodies. Protein-A Sepharose CL-4B resin (Pharmacia) was added for one hour at 4° C. and subsequently rinsed twice with RIPA/PMSF. The samples were reconstituted in non-reducing Laemmli sample buffer, boiled for five minutes, and analyzed by SDS-PAGE (14% acrylamide).

Growth in serum and platelet poor plasma (PPP). The PDGF-A, c-sis, and pMT2 primary transfected cell lines were plated in 10% BCS at a density of 2000 cells/cm² into 24-well plates. After 24 hours, the media was changed to either 5% BCS or 5% platelet poor plasma (PPP) and new media added every third day. Duplicate wells were trypsinized and counted using a Coulter counter (Coulter Electronics, Inc.) and the average number of cells per cm² recorded daily for 8 days. Cells transfected with the dominant negative mutants were similarly plated into 6-well dishes also, at a starting density of 2000 cells/cm².

Colony formation assay. Cells were transfected with the dominant negative mutants as described above. Following the transfection, cells were grown in 10% BCS for 24 hours and then split 1:2 into either 5% BCS or 5% PPP with 500 µg/ml neomycin sulfate and 200 pg/ml hygromycin B. For transfection of astrocytoma cells, the media was changed to 5% PPP and 500 µg/ml neomycin sulfate 48 hours after transfection for simultaneous selection of drug resistance and growth in PDGF-deprived media. After approximately three weeks, drug resistant colonies were photographed at 10xmagnification or fixed with 10% formalin and stained with 0.625% crystal violet for analysis.

Anchorage-independent growth. Sterilized 1.8% agar in water was mixed with equal volumes of 2xDMEM+20% BCS, layered on the bottom of 60 mm diameter culture dishes (Falcon), and allowed to gel at RT. A methocellulose suspension with 1xDMEM+10% BCS was prepared as previously described (Risser et al., Virology 59:471–489, 1974). A suspension of $10^5$ cells in 4 ml of methocellulose/BCS was layered on top of the agarose bed. Fresh methocellulose/BCS (3 ml) was added weekly. The number of colonies that grew in suspension were qualitatively evaluated.

Western immunoblotting. Cells were grown to confluence in 150 mm dishes and incubated in 5% PPP for 48 hours. As controls, Balb/c 3T3 cells were incubated for 15 minutes in the absence or presence of 30 ng/ml PDGF-AA or PDGF-BB (UBI). Cellular protein was isolated at 4° C. with 0.5 ml of lysis buffer (10 mM NaP buffer pH 7.2, 150 mM NaCl, 1% Nonidet P-40, 10% glycerol, 0.2% NaF, 0.44% NaPPi) containing 1 mM Na-orthovanadate, 5 µg/ml aprotinin, and 1 mM PMSF. The lysates were microfuged to remove cellular debris. The protein content was quantified (Biorad Protein Analysis) and the lysates stored at −70° C.

For anti-PDGF-α receptor blots, PDGF-A transformed (~300 µg) or wildtype 3T3 (~150 µg) cell lysates were resuspended in reducing Laemmli (1x) buffer, boiled for 5 minutes, and separated on 7.5% SDS polyacrylamide gels. The gels were transblotted to nitrocellulose and blocked at 37° C. with 2% gelatin in TBS (10 mM Tris pH 8.0, 0.9% NaCl) for 1 hour. A polyclonal anti-PDGF-α receptor antibody (kindly provided by Chiayeng Wang, diluted 1:100 in TBST) or a monoclonal anti-phosphotyrosine antibody (kindly provided by Thomas Roberts, diluted 1:5000) was applied overnight at RT. For anti-PDGF-β receptor blots, c-sis transformed (~3000 µg) or wildtype 3T3 (~30 µg) cell lysates were first enriched for PDGF-β receptors by immunoprecipitation (as outlined above) with a polyclonal anti-PDGF-β-receptor antibody (1:100, Upstate Biotechnology Inc.) prior to Western blotting. The immunoprecipitates were resuspended in reducing Laemmli buffer, boiled for 5 minutes, and separated on 7.5% SDS polyacrylamide gels. The gels were transblotted to Immobilon-P (Millipore) and blocked at RT with 5% bovine serum albumin in PBS for 2 hours. Anti-PDGF-β receptor antibody or anti-phosphotyrosine antibody (both diluted 1:5000 in blocking buffer) was applied for 1.5 hours at RT. After rinsing with TBST, the secondary anti-rabbit or anti-mouse alkaline-phosphatase conjugated antibody (1:7000, Promega) was applied for 1 hour at RT in TBST. Alkaline phosphatase reactions were carried out with the addition of 66 µl nitro blue tetrazolium and 33 µl 5-bromo-4-chloro-3-indolyl phosphate to 10 ml of developing buffer (100 mM Tris pH 9.5, 100 mM NaCl, 5 mM MgCl$_2$). Cell lysates used in all immunoprecipitations and immunoblots were normalized on the basis of total protein content.

Figure 3A:
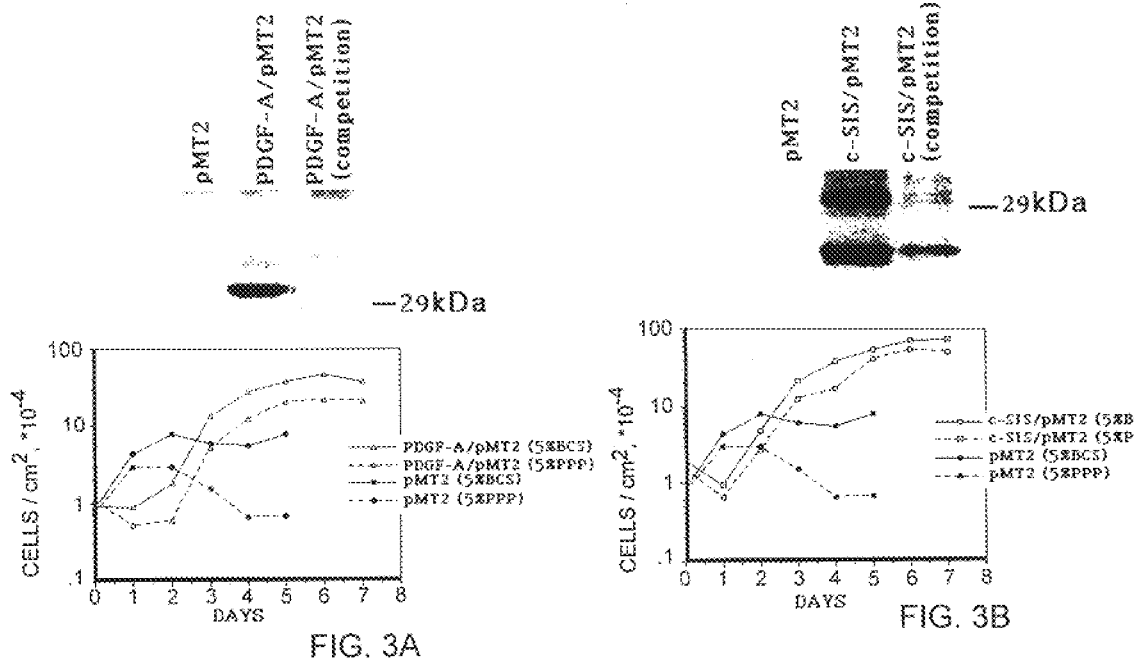
FIGS. 3A and 3B are immunoprecipitations of conditioned media from PDGF-A transformed cells (FIG. 3A) and cell lysates from c-sis transformed cells (FIG. 3B) carried out with PDGF-AA or PDGF-BB specific antibodies, respectively, in the absence and presence unlabeled competitor. The graphs show the growth of PDGF-A (FIG. 3A) and c-sis (FIG. 3B) transformed cells in 5% bovine calf serum (BCS) versus 5% platelet-poor plasma (PPP) measured at the indicated days.
Figure 3B:
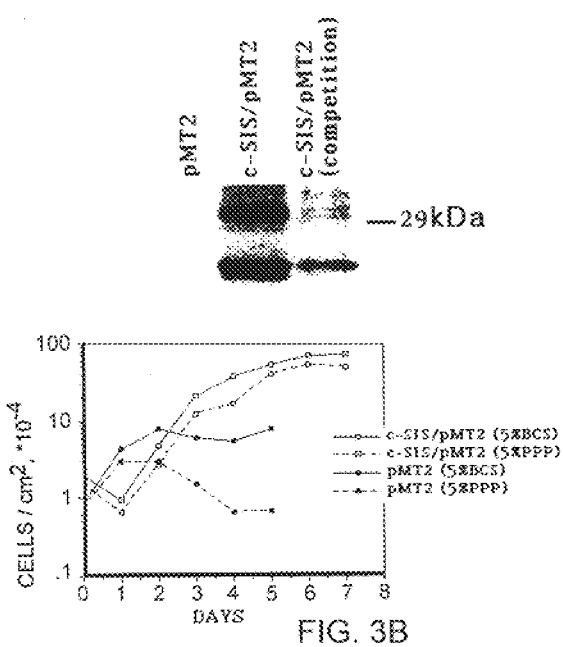

Nude mice. Pooled colonies of U343 astrocytoma cells transfected with the 1308 dominant negative mutant or the control expression vector (pLNCX), were trypsinized and resuspended in DMEM. Using a tuberculin syringe and a 27 gauge hypodermic needle, $10^7$ cells (0.3 ml) were injected into the subcutaneous interscapular tissue of 4 to 6 week old male Swiss nude mice (Taconic). The tumor diameter was recorded for four animals per experimental set on a weekly basis starting at 3 weeks postinjection. The mean tumor diameter +/− standard error of the mean was calculated, and the statistical significance at 10 weeks was determined by Student's t test (STAT_SAK; G. E. Dallal). Results Transformation of BALB/c 3T3 cells with PDGF-A or PDGF-B (c-sis) enhances cell growth in PDGF-deficient medium. PDGF-A or PDGF B (c-sis) cDNAs were subcloned into the pMT2 expression vector and co-transfected with the hygromycin B resistance plasmid, pY3, into Balb/c 3T3 fibroblasts. Two hygromycin B resistant sublines expressing high levels of PDGF-A or B mRNA were selected for further characterization. One cell line produces PDGF-AA homodimer and releases it into the cell culture medium (FIG. 3A). Another produces PDGF-BB homodimer, the bulk of which remains cell associated, as noted by others (LaRochelle et al., Genes Dev. 5:1191–1199, 1991) (FIG. 3B). Both of the PDGF producing sublines were released from their growth-dependence on exogenous PDGF (FIGS. 3A and 3B). This release was demonstrated by comparing cell growth in medium supplemented with platelet-poor plasma (PPP) to growth in medium supplemented with bovine calf serum (BCS). As the product of unclotted blood, PPP contains little, if any, PDGF (Singh et al., J. Cell Biol. 95:667–671, 1982; Bowen-Pope et al., J. Biol. Chem. 264:2502–2508, 1989). Cells transformed with either PDGF A or PDGF B (c-sis) grew nearly as well in PPP or BCS-supplemented medium. By contrast, a control culture of Balb/c 3T3 cells, transfected with vector alone, shows superior growth in the BCS-supplemented medium. In addition to reducing the growth differential between PPP and BCS-supplemented medium, transformation with either PDGF A or PDGF B (c-sis) increased the final cell density at confluence (FIGS. 3A and 3B).

PDGF dominant negative mutants restore serum dependence of 3T3 cells transformed by PDGFs. The PDGF-A and PDGF-B (c-sis) transformed 3T3 cell sublines were subjected to secondary transfections with expression vectors encoding either of two PDGF dominant negative mutants, 1317 or 1308. Two subclones from each transfection group which expressed high levels of 1317 or 1308 mRNA were selected for further study. First, the secondary transfectants were tested for growth in PPP-supplemented medium. Expression of either mutant suppressed the growth of PDGF-A transformed sublines (by approximately 70%) as compared to a control PDGF-A transformed subline which received only the pLNCX vector during secondary transfection (FIG. 4A). The PDGF-B (c-sis) transformed sublines expressing 1308 were likewise growth-inhibited (by approximately 90%) as compared to the control PDGF-B (c-sis) transformed subline (FIG. 4B). The 1317 mutant failed to suppress the growth of c-sis transformed cells and, in fact, facilitated growth, consistent with previous findings which suggested that the 1317:PDGF-B heterodimer retains functional activity (Mercola et al., Genes Dev. 4:2333–2341, 1990). The inhibition of growth by 1308 and 1317 is specific to PDGF transformed cells, as they were unable to inhibit the growth of Ha-ras transformed Balb/c 3T3 cells (FIG. 4C).

Figure 5:
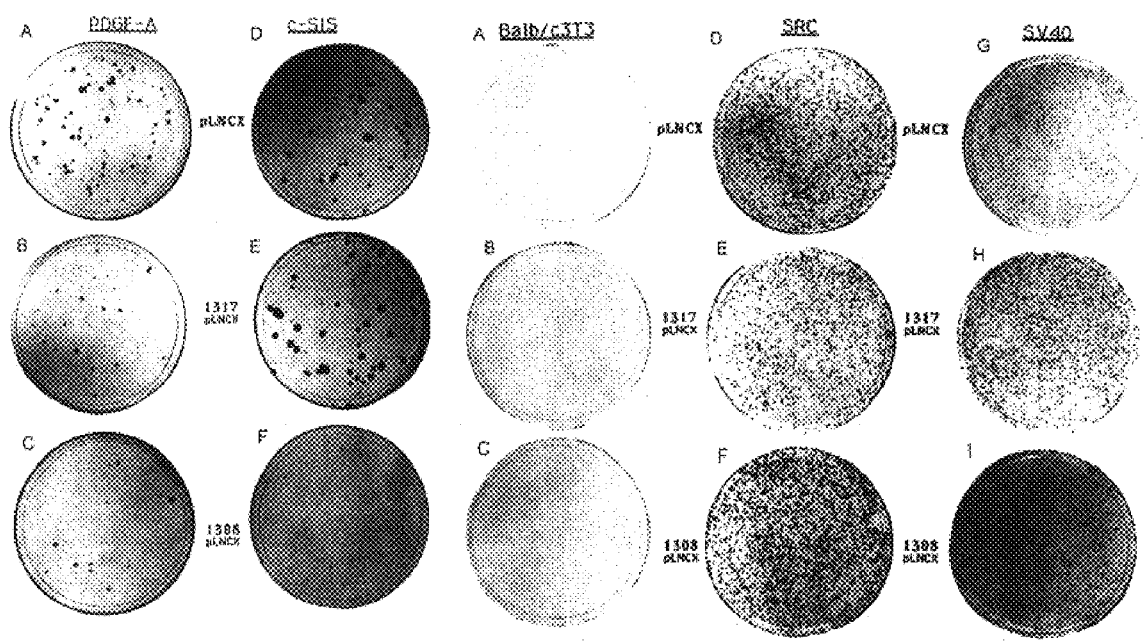
FIG. 5 is a photograph of a colony formation assay of PDGF-A, PDGF-B (c-sis), v-src, and SV40 transformed Balb/c3T3 cells transfected with the dominant negative mutants indicated.

A colony formation assay for the action of PDGF dominant negative mutants. To eliminate the possibility of clonal selection bias and to rapidly screen other cell lines, a colony formation assay for growth in PDGF-free medium was used. The dominant negative mutant expression vectors were transfected into 3T3 cells which had been transformed with PDGF-A, PDGF-B (c-sis), or two unrelated oncogenic agents, v-src and SV40. Transfected cells were selected for neomycin resistance in PPP-supplemented medium. Under these conditions, only cells which have escaped the requirement for exogenous PDGF yield macroscopically visible colonies (Armelin et al., Nature 310:655–660, 1984; Zhan et al., Mol. Cell. Biol. 6:3541–3544, 1986). As expected, wildtype Balb/c 3T3 cells failed to form colonies in PPP-supplemented medium, whereas cells transformed by PDGF-A, PDGF-B (c-sis), v-src, or SV40 did form colonies (FIG. 5). Transfection with either 1317 or 1308 reduced the number and average size of PDGF-A transformed cell colonies (FIG. 5). Only the 1308 mutant suppressed colony formation of cells transformed by PDGF-B (c-sis) (FIG. 5). The 1308 and 1317 mutants neither suppressed nor enhanced colony formation of v-src or SV-40 transformed cells (FIG. 5). As noted in growth rate measurements (FIG. 4), and in accord with previous transfection studies on COS cell cultures (Mercola et al., Genes Dev. 4:2333–2341, 1990), 1317 actually enhanced the number and average size of colonies of cells transformed with PDGF-B (c-sis).

Dominant negative mutants inhibit anchorage-independent growth of PDGF transformed 3T3 cells. One hallmark of transformed cell lines is the ability to develop colonies in soft agar or methocellulose suspension. The PDGF-B (c-sis) transformed cells developed large colonies (approximately 50 cells or greater) growing in a methocellulose suspension within 14 days (FIG. 6). Expression of 1308 in these cells inhibited growth in methocellulose. In agreement with results in two different growth assays (FIGS. 4 and 5), expression of 1317 actually enhanced anchorage-independent growth of the PDGF-B (c-sis) transformed cells. The PDGF-A transformed 3T3 cells also developed colonies in methocellulose suspension, albeit smaller than the ones generated by PDGF-B (c-sis) transformed cells (FIG. 6). Expression of either 1308 or 1317 in PDGF-A transformed cells inhibited anchorage-independent growth, in accord with the growth rate measurements and colony formation assays (FIGS. 4 and 6).

Figure 7A:
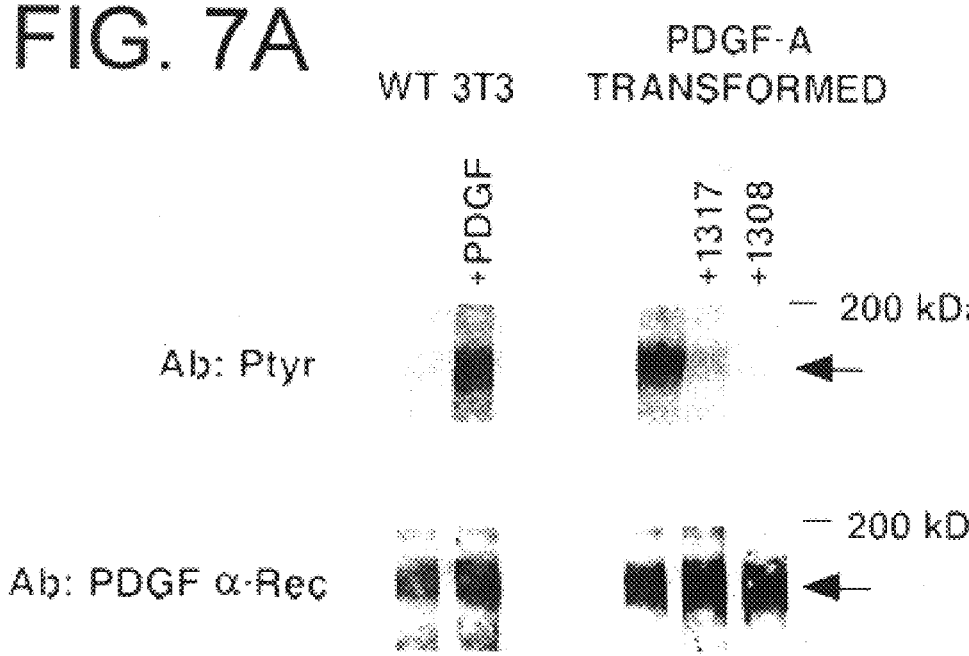
FIGS. 7A and 7B are immunoblots of cell lysates of wildtype 3T3 cells (untreated or +PDGF), PDGF-A transformed cells (untreated or transfected with 1317 or 1308) (FIG. 7A), and PDGF-B (c-sis) transformed cells (untreated or transfected with 1308) (FIG. 7B) probed with anti-phosphotyrosine, anti-PDGF-α receptor, or anti-PDGF-β receptor antibodies, as indicated.
Figure 7B:
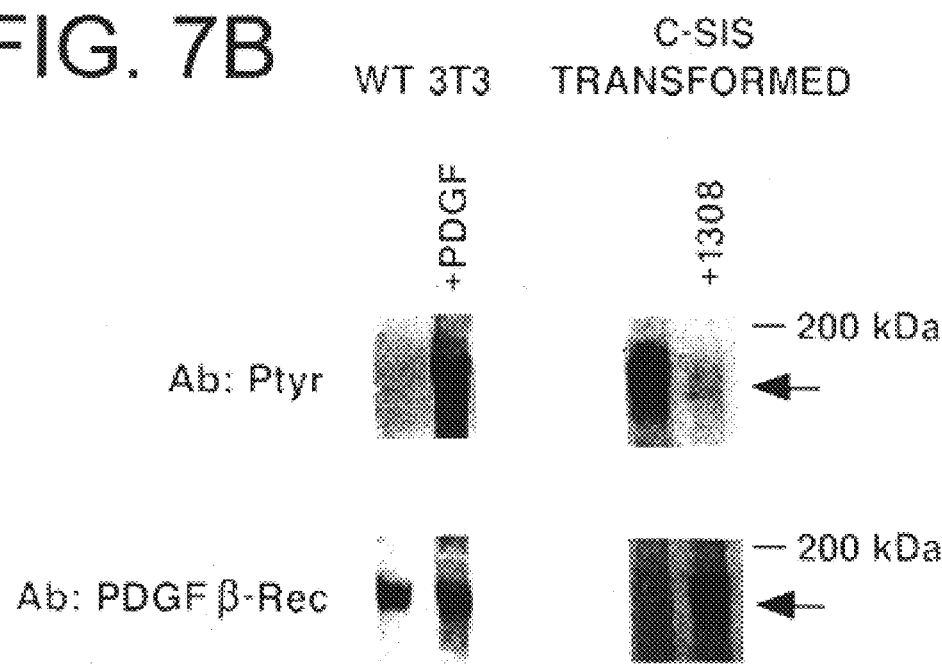

Disruption of PDGF autocrine loops by the dominant negative mutants. The tyrosine phosphorylation status of PDGF receptors was examined by Western immunoblotting with an anti-phosphotyrosine antibody. When normal 3T3 cells are cultured in PPP-supplemented medium, the PDGF receptors are not phosphorylated unless challenged with exogenous PDGF. In the same medium, receptors are constitutively tyrosine phosphorylated in cells transformed with PDGF-A or PDGF-B (c-sis) (FIGS. 7A and 7B). Expression of the 1308 mutant eliminated this constitutive tyrosine phosphorylation in either PDGF-A or PDGF-B (c-sis) transformed cells (FIGS. 7A and 7B). In keeping with its biologic and biochemical action spectrum, expression of 1317 eliminated the constitutive phosphotyrosine signal in cells transformed by PDGF-A (FIG. 7A) but not PDGF-B (c-sis) (FIG. 7B). Western immunoblotting with anti-PDGF-α and anti-PDGF-β receptor antibodies showed that loss of the constitutive tyrosine phosphate signal on PDGF receptors did not reflect a loss of PDGF receptor protein. Indeed, total receptor protein was more abundant following transfection with dominant negative mutants. This apparent upregulation was especially evident in the PDGF-B (c-sis) transformed cells following transfection with 1308 (FIG. 7B).

Taken together, these data indicate that PDGF autocrine loops are closed in 3T3 cells that express either PDGF-A or B and that the dominant negative mutants disrupt these loops. It should be noted, however, that acquisition and reversion of the transformed phenotype do not correlate in a linear way with the abundance of tyrosine phosphorylated PDGF receptor. The total abundance of PDGF receptor protein in PDGF-B (c-sis) transformed 3T3 cells is less than one percent that of control 3T3 cells (see FIG. 7). By extension, there is probably less tyrosine phosphorylated PDGF receptor in the aggressively growing, transformed cells than in the quiescent, growth arrested 3T3 controls. Although receptors are upregulated when PDGF autocrine loops are broken by our dominant negative mutants they do not return to the levels seen in wildtype 3T3 cells.

Figure 8A:
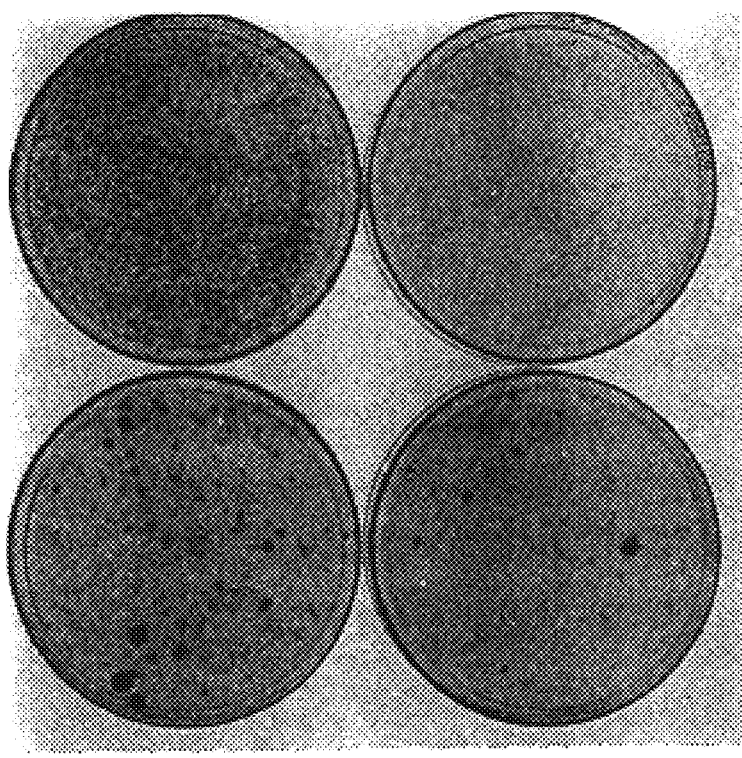
FIG. 8A is a photograph of a colony formation assay of U343 and U87 cells transfected with dominant negative mutant 1308 or vector alone.
Figure 8B:
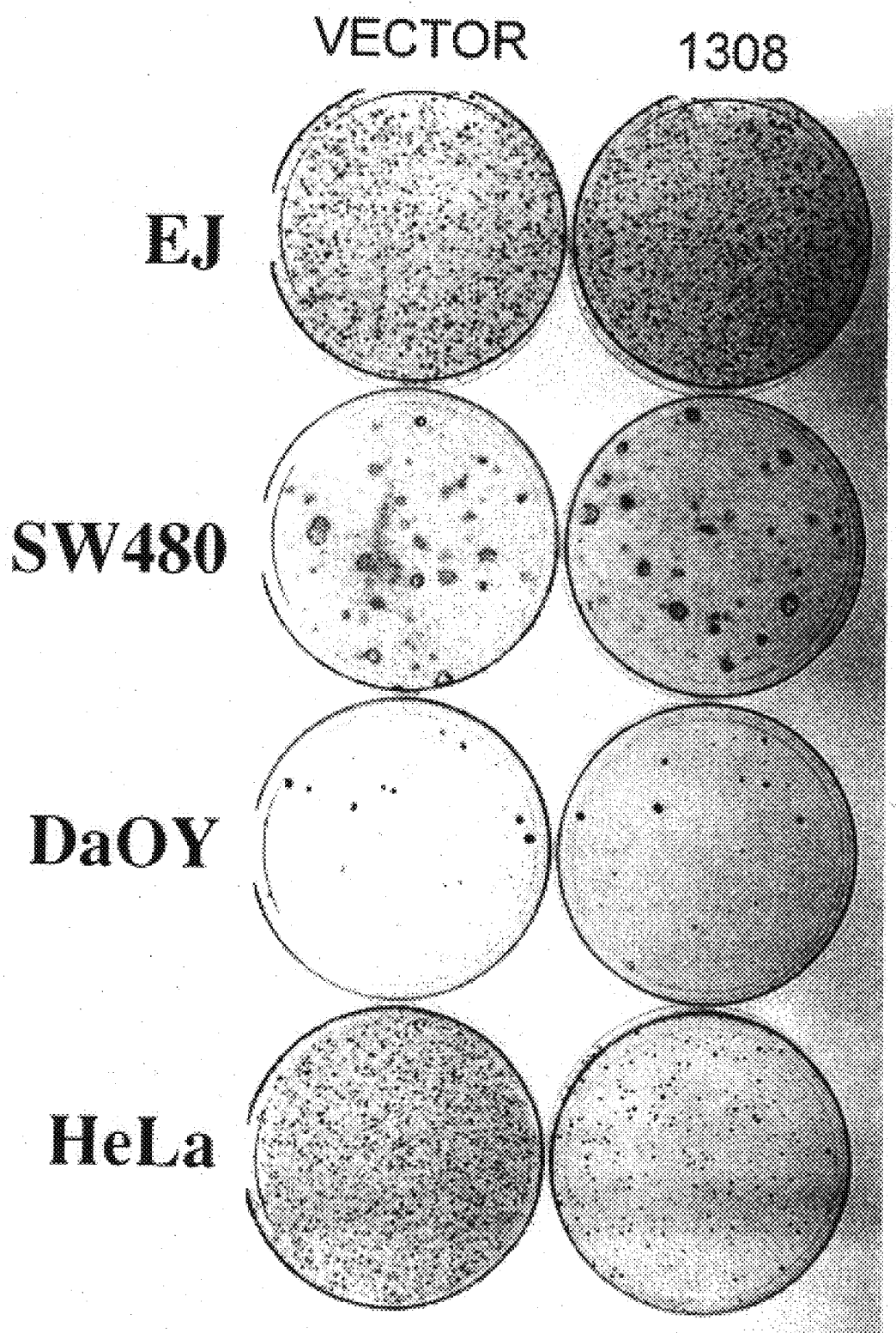
FIG. 8B is a photograph of a colony formation assay of EJ, SW480, DaOY, and HeLa cells transfected with dominant negative mutant 1308 or vector alone.

Inhibition of astrocytoma cell growth by the 1308 dominant negative mutant. Of the two mutants we characterized, only 1308 was active on both PDGF A and PDGF-B (c-sis) transformed 3T3 cells. For this reason, 1308 was expressed in two independent astrocytoma cell lines, U87 MG (U87) and U343 MGa Cl 2:6 (U343). These cell lines were previously characterized and found to express both PDGF-A and PDGF-B together with PDGF-β receptors; U343 expresses higher levels of the ligands whereas U87 expresses more receptors (Nister et al., J. Biol. Chem. 266:16755–16763, 1991). Based on these expression patterns, both cell lines are candidates for possessing PDGF autocrine loops. Using the colony formation assay described above (FIG. 5), it was found that both U87 and U343 cells formed colonies in PPP-supplemented medium. Thus, as predicted, these cells do not require exogenous PDGF for growth (FIG. 8A). When either astrocytoma line was transfected with 1308, colony formation in PPP-supplemented medium was markedly inhibited (FIG. 8A). As controls for specificity, the response of one human cell line derived from a different type of brain tumor (the medulloblastoma cell line, DaOY) and two human tumor cell lines that express an activated ras gene were studied (the EJ bladder carcinoma line and the SW480 colon carcinoma). None of these cell lines were affected by 1308 (FIG. 8B). All five of these human cell lines were shown to express equivalent amounts of 1308 mRNA.

Figure 9A:
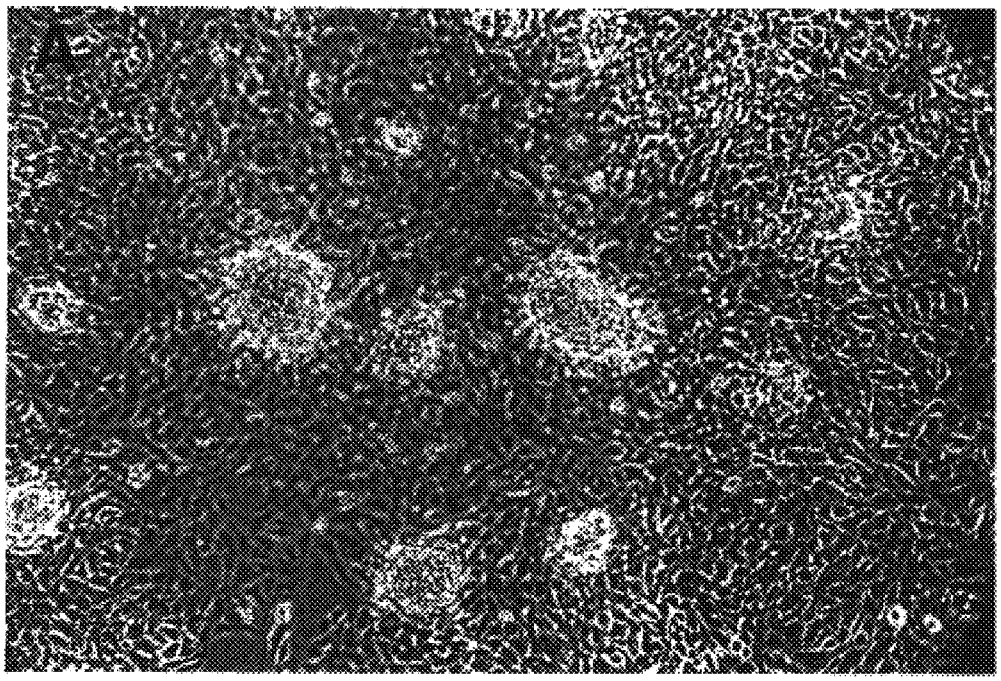
FIG. 9A is a photograph of U343 astrocytoma cells transfected with the control expression vector at 10×magnification.
Figure 9B:
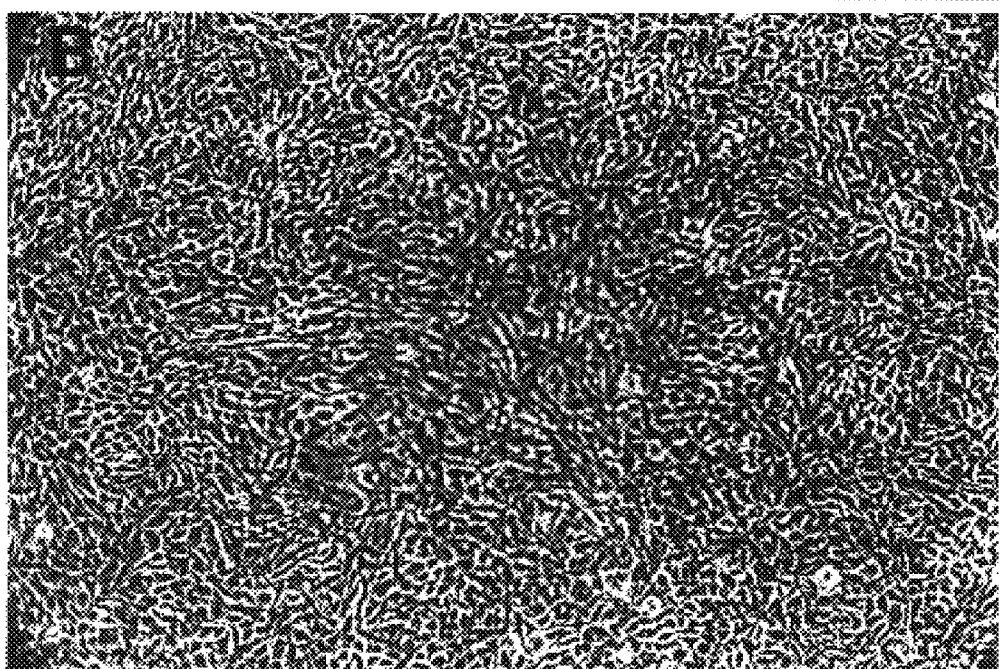
FIG. 9B is a photograph of U343 astrocytoma cells transfected with PDGF dominant negative mutant 1308 at 10×magnification.

Morphological changes in astrocytoma cells. The U343 and the U87 astrocytoma cell lines form multilayered, refractile foci when grown in culture. Expression of the 1308 mutant in either cell line resulted in distinct morphological changes. Both the number and size of foci that developed when grown in PPP-supplemented medium were reduced relative to control cells transfected with vector alone (FIG. 9). In the case of U87 cells, expression of 1308 prevented the formation of subconfluent foci, a characteristic of this cell line. When the growth period was extended, U87 cells expressing 1308 ultimately developed foci that were smaller and delayed compared to control cells. It is important to note that 1308 did not affect the viability of these cells. We never observed cell debris, cytoplasmic vacuoles or other visual indicators of a toxic response to 1308 expression. All cells expressing the dominant negative mutant remained capable of sustained growth in serum and PPP-supplemented medium, albeit at slower rates than control cells.

Figure 10:
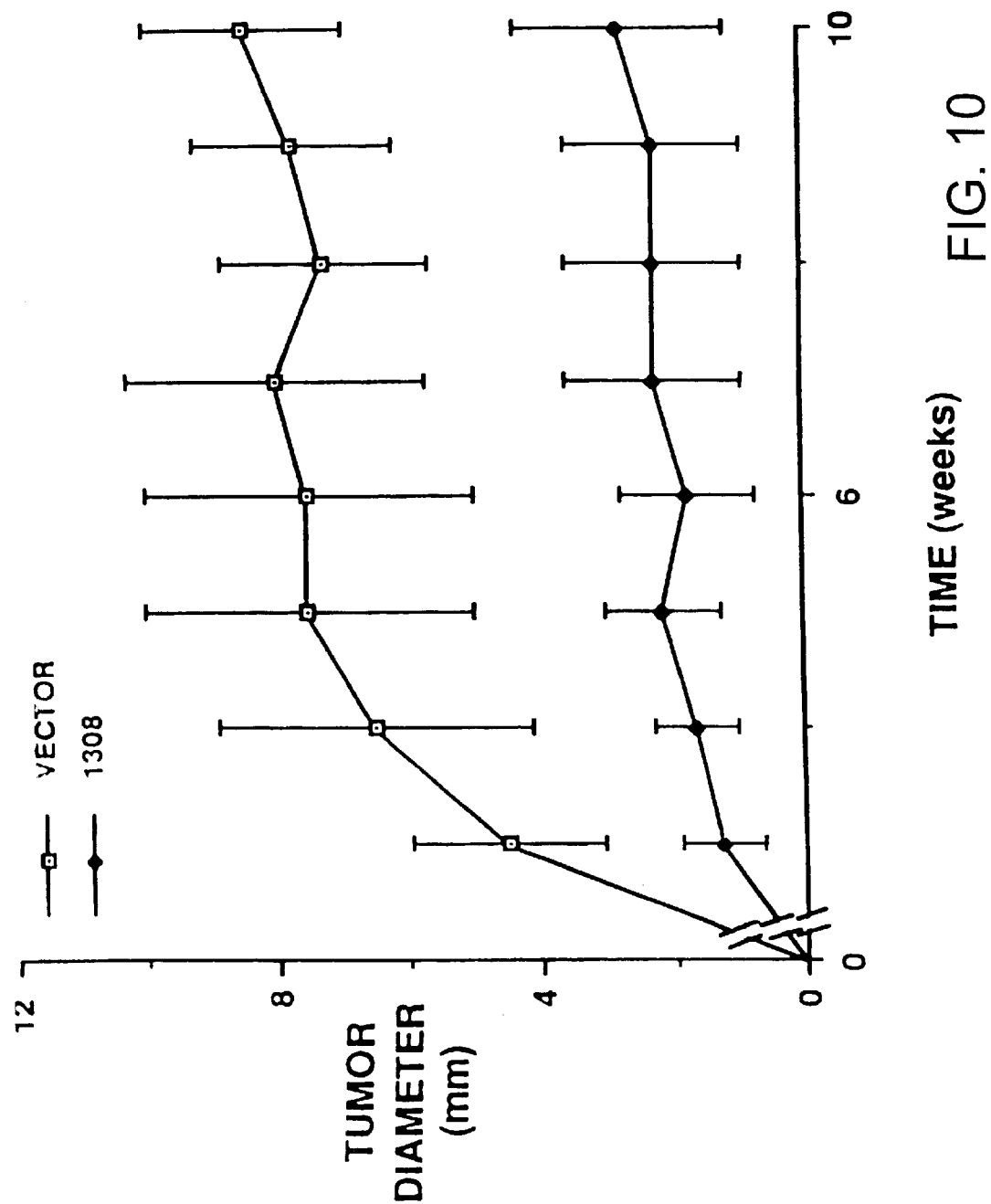
FIG. 10 is a graph of the diameters of tumors produced in nude mice injected with U343 astrocytoma cells transfected with the control expression vector or 1308.

Decreased tumorigenicity in nude mice of astrocytoma cells expressing 1308. U343 cells expressing 1308 were injected into nude mice as a measure of the tumorigenicity of these cells. Each of four mice injected in the intrascapular region with the control U343 cells developed moderate size tumors that persisted through ten weeks (FIG. 10). In contrast, U343 cells expressing the 1308 dominant negative mutant induced small tumor formation in only two of four injected mice. At ten weeks, the mean diameter of tumors formed by U343 cells was reduced by 70% in cells expressing 1308 (t=2.6, p<.05).

What is claimed is:

1. A eucaryotic trans-dominant suppressor gene encoding a protein translation product which suppresses the activity of a growth factor that requires an oligomeric state for function, by forming an inactive oligomer with a wildtype subunit of said growth factor, said protein translation product being a mutant form of a wildtype subunit of said growth factor.

2. The gene of claim 1, wherein said protein translation product is a mutant form of a PDGF subunit having a modification in the amino acid sequence of the proteolytic cleavage site of said PDGF subunit, said modification preventing proteolytic cleavage at said site.

3. The gene of claim 1, wherein said protein translation product is a mutant form of a PDGF subunit, wherein one of the cysteine residues essential for the mitogenic activity of PDGF is replaced with a different amino acid, and at least one other cysteine residue remains unmodified.

4. A vector comprising the trans-dominant suppressor gene of claim 1.

5. The vector of claim 4, wherein said trans-dominant suppressor gene is operably linked to a functional promoter.

6. The vector of claim 4, wherein said vector is a viral vector.

7. The vector of claim 4, wherein said vector is a retrovirus, adenovirus, adeno-associated virus, SV40 virus, or herpes virus.

8. A cell comprising the gene of claim 1.

9. The cell of claim 8, wherein said cell expresses a eucaryotic trans-dominant suppressor from said gene.

10. An essentially homogeneous population of cells, each of which comprises the gene of claim 1.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Mus musculus

<400> SEQUENCE: 1

Arg Arg Lys Arg
 1

<210> SEQ ID NO 2
<211> LENGTH: 6
<212> TYPE: PRT
<213> ORGANISM: Mus musculus

<400> SEQUENCE: 2

Ser Arg His Arg Arg Ala
 1               5

<210> SEQ ID NO 3
<211> LENGTH: 6
<212> TYPE: PRT
<213> ORGANISM: Mus musculus

<400> SEQUENCE: 3

Ser Gln His Ser Gly Ala
```

```
<210> SEQ ID NO 4
<211> LENGTH: 6
<212> TYPE: PRT
<213> ORGANISM: Mus musculus

<400> SEQUENCE: 4

Arg Arg Lys Lys Arg Ala
 1               5

<210> SEQ ID NO 5
<211> LENGTH: 6
<212> TYPE: PRT
<213> ORGANISM: Mus musculus

<400> SEQUENCE: 5

Arg Gln Asn Gln Gly Ala
 1               5

<210> SEQ ID NO 6
<211> LENGTH: 6
<212> TYPE: PRT
<213> ORGANISM: Mus musculus

<400> SEQUENCE: 6

Ile Arg Arg Lys Arg Ser
 1               5

<210> SEQ ID NO 7
<211> LENGTH: 18
<212> TYPE: DNA
<213> ORGANISM: Mus musculus

<400> SEQUENCE: 7
attcgcagga agagaagt                                                  18
```